Jan. 12, 1971 L. T. POWELL Plant Pat. 3,015
PEACH TREE
Filed July 12, 1968
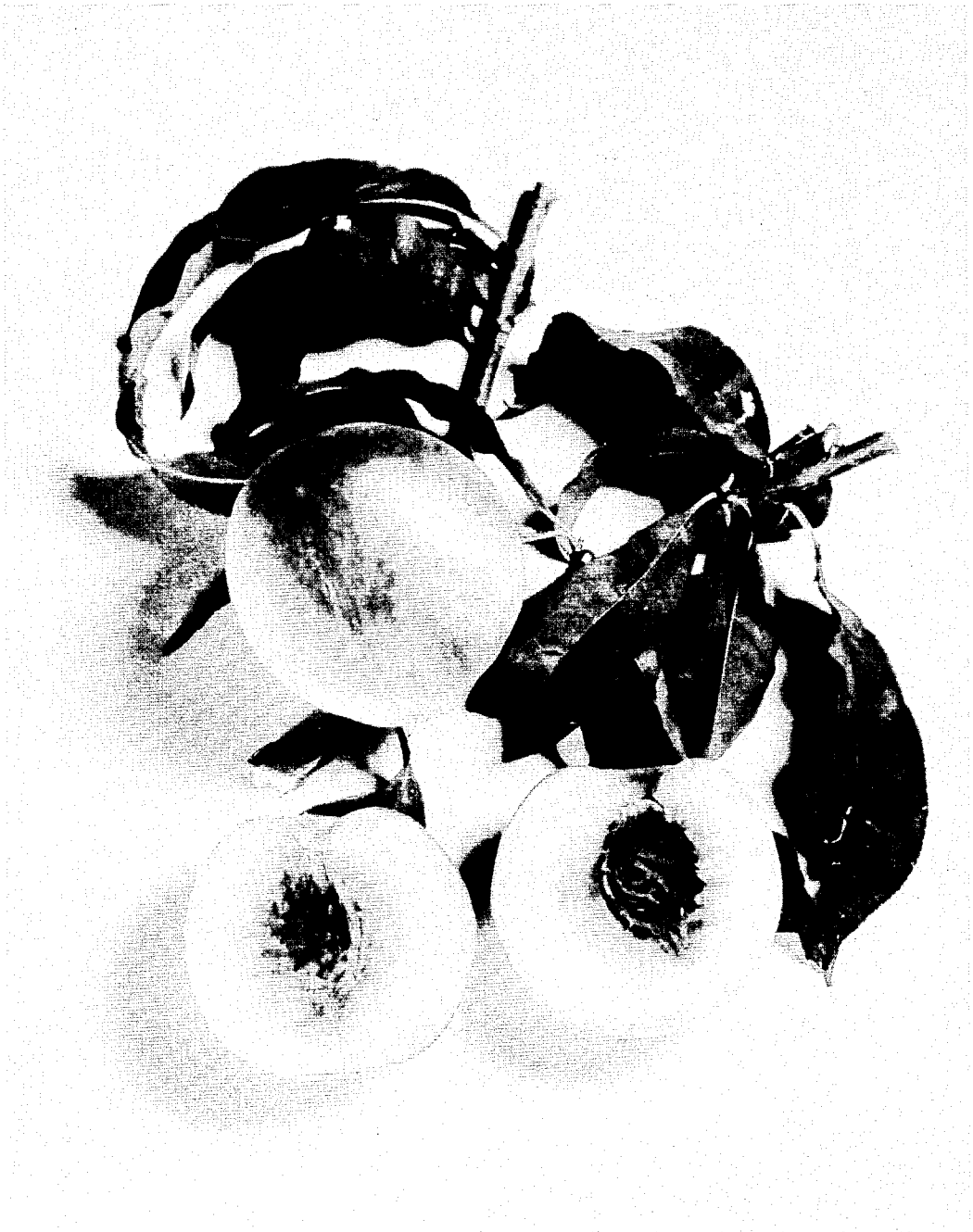
INVENTOR
Lewis Thornton Powell
BY
Webster & Webster
ATTORNEYS United States Patent Office Plant Pat. 3,015
Patented Jan. 12, 1971

3,015

PEACH TREE

Lewis Thornton Powell, 8016 N. Winton Way,
Winton, Calif. 95388

Filed July 12, 1968, Ser. No. 744,592
Int. Cl. A01h 5/00
U.S. Cl. Plt.—43 1 Claim

ABSTRACT OF THE DISCLOSURE

A variety of peach tree, of medium size, moderately spreading form, and moderately vigorous growth, which is a regular and very productive bearer of large, relatively uniform freestone fruit having firm flesh, and skin tenacious to the flesh when the fruit is firm ripe; the flesh being an apricot yellow, the pit cavity red which streaks into the flesh, and the skin yellow, partially overspread with red.

BACKGROUND OF THE VARIETY

For the fresh fruit market (both local and distant), and for processing by freezing, it is desirable that peach fruit be uniform in shape to provide an attractive appearance as well as to facilitate processing, firm fleshed to permit handling when mature without serious bruising, and relatively resistant to oxidation and resultant browning upon thawing after freezing; the fruit preferably having yellow flesh with a red pit cavity.

ORIGIN OF THE VARIETY

The herein claimed variety of peach was discovered by me under the following factual circumstances:

Being a producer and shipper of peaches for both the fresh fruit market and for frozen food processing, and being cognizant of the type of peach preferred for such purposes as hereinbefore noted, I was aware of the need of a variety of peach tree whose fruit would better meet such requirements, especially for freezing, than the fruit of any previously known variety. Therefore, I continuously observed the characteristics of any spontaneous mutation which developed in my peach orchards, preserving any such mutations—that appeared to have possible merit—by permitting selected mutation twigs to develop into fruiting "hangers" on the parent tree, and then observing their fruit and productivity in succeeding years. Of the many such mutations observed and permitted to bear fruit, one (which occurred on a tree of the Kirkman Gem (U.S. Plant Pat. No. 506)) appeared—upon continuing observation—to have the aforementioned desirable characteristics. I, therefore, selected such one mutation for asexual reproduction, preparatory to commercialization thereof; such selection being the herein claimed variety.

ASEXUAL REPRODUCTION OF THE VARIETY

Subsequent to my discovery of the variety in the manner described above, I asexually reproduced it in one of my orchards located near Winton, Merced County, Calif., by June budding—in accordance with accepted nursery practice—on Lovell (unpatented) seedlings with buds taken from the parent (mutant) limb on the aforesaid Kirkman Gem tree. Such asexual reproductions were, in maturity, found to run true to the parent in all respects.

SUMMARY OF THE VARIETY

The present variety of peach tree, which is of medium size, moderately spreading form, and moderately vigorous growth, is a regular and very productive bearer of large, relatively uniform, freestone fruit having firm flesh to which the skin is tenacious when the fruit is firm ripe; the flesh being an apricot yellow, the pit cavity red which streaks into the flesh, and the skin yellow, partially overspread with red.

The present variety of peach tree, while having general resemblance—in tree and fruit—to the Rio Oso Gem (U.S. Plant Pat. No. 84), is, in comparison, characterized by the following advantageous distinctions:

(1) The fruit, which ripens two or three days earlier than the Rio Oso Gem, is much more symmetrical in shape; the halves, when cut on a plane through the suture, being nearly equal.

(2) The fruit is firmer of flesh, and, when cut, is particularly resistant to oxidation and resultant browning, so that the fruit is especially adapted to freezer processing.

(3) The fruit is sweeter of flesh, and which flesh is smoother textured and less fibrous.

Both grown under similar conditions, the tree habit, wood, and leaves of the present variety of peach tree are similar to the parent Kirkman Gem but substantial distinctions otherwise exist. More particularly, the tree of the Kirkman Gem is not vigorous in growth while the present variety evidences moderate vigor; and the fruit of the present variety—which ripens about one month earlier—is more symmetrical in shape in that the fruit halves are approximately equal rather than one half larger than the other as in the Kirkman Gem. Further, the firm flesh (tart) of the Kirkman Gem evidences some stringiness while the flesh (sweet) of the present variety is mellow and smooth-textured. Additionally, the Kirkman Gem has a pronounced suture stripe with the flesh not joined, whereas the present variety has no such stripe and the flesh is joined—thus being less susceptible to deterioration in storage or shipment.

BRIEF DESCRIPTION OF THE DRAWING

The drawing comprises an illustration, by photographic reproduction in color, of a twig with leaves and attached fruit; another fruit being shown cut in half with the halves disposed to expose the flesh and with the stone remaining in place in one such half.

DESCRIPTION OF THE VARIETY

The botanical details of this new and distinct variety of peach tree—with color definitions (except those in common color terms) referenced to Maerz and Paul Dictionary of Color—are as follows:

Tree:
- *Size.*—Medium.
- *Virgor.*—Moderate.
- *Growth.*—Spreading.
- *Production.*—Very productive.
- *Bearing.*—Regular bearer.

Trunk:
- *Size.*—Stocky.
- *Texture.*—Medium.

Branches: Branches freely.

Leaves:
- *Size.*—Medium. Length: 5" to 7"; average 6". Width: 1⅜" to 1⅝"; average 1½".
- *Form.*—Lanceolate, with tip acuminate.
- *Thickness.*—Medium.
- *Glands.*—Reniform. Positioned on base of blade.
- *Margin.*—Crenate.
- *Color.*—Top side: Medium green (23–J–8). Underside: Lighter green (22–J–6), with still lighter green midrib.

Flower buds:
- *Size.*—Medium.
- *Form.*—Ovate. Plump. Free.

Flowers:

*Size.*—Large. Showy.

*Color.*—Pink.

*Fertility.*—Pollen fertile.

Fruit:

*Maturity when described.*—Firm ripe.

*Ripening dates.*—1965: Aug. 15–Aug. 20, 1966: Aug. 15–Aug. 20, 1967: Aug. 25. In each year the fruit ripened approximately 2 to 3 days earlier than the Rio Oso Gem.

*Size.*—Large. Axial diameter: 2⅝" to 3⅛"; average 3". Transversely in suture plane: 2⅝" to 3⅜"; average 3". At right angles to suture plane: 2⅝" to 2⅞"; average 2¾".

*Form.*—Generally truncate; oval in cheek aspect; ovate in suture aspect.

*Ventral surface.*—Lightly lipped on one side.

*Ventral suture.*—Somewhat rough. Corky in 1967, but in previous years very little cork or roughness.

*Cavity.*—Flaring to rounded. Slightly elongated in suture plane. Depth: 7/16" to ⅝"; average 9/16". Breadth: 15/16" to 1 1/16"; average 1". Markings: Yellow, with some red.

*Base.*—Truncate, mostly at right angles to axis.

*Pistil point.*—Apical, usually not fleshy.

*Stem.*—Short; approximate length ¼". Usually free from stone at maturity.

Skin:

*Thickness.*—Medium.

*Tenacity.*—Tenacious to flesh when firm ripe.

*Tendency to crack.*—None.

*Down.*—Moderate.

*Color.*—Light greenish yellow (18–J–4) to light yellow (9–I–6), partially overspread with red (5–J–5 to 6–J–5).

Flesh:

*Amygdalin.*—Scant, practically no browning of cut fruit.

*Juice.*—Moderate.

*Texture.*—Firm. Meaty. Granular.

*Fibers.*—Moderate. Fine. Tender.

*Ripens.*—Evenly.

*Flavor.*—Subacid. Mild. Sweet.

*Aroma.*—Moderate. Pleasant.

*Eating quality.*—Excellent.

*Color.*—Apricot yellow (9–K–5). Surface of pit cavity: red (6–L–6), streaked into flesh, especially at suture line.

Stone:

*Type.*—Free.

*Fibers.*—Few and short near base, otherwise lacking.

*Size.*—Medium. Length: 1¼" to 1 7/16"; average 1 5/16". Breadth: 1" to 1 1/16"; average 1". Thickness: ¾" to 1 1/32"; average ¾".

*Form.*—Obovate, with acuminate tip.

*Base.*—Small, at right angles to axis.

*Hilum.*—Oval.

*Apex.*—Cuspidate.

*Sides.*—Equal.

*Surface.*—Irregularly pitted and furrowed, pitted toward base, furrowed toward apex.

*Ventral edge.*—Medium thickness, with deep furrows on each side.

*Dorsal edge.*—Moderately deep, broken furrow.

*Tendency to split.*—Slight in 1967 when other peaches suffered heavy split pits.

*Color.*—Deep brown (7–H–11).

Use: Culinary. Market—local and long distance shipping. Freezing.

Keeping quality: Very good.

Resistance to insects and disease: Average, but apparently somewhat resistant to mildew.

Shipping quality: Good:

The peach tree and its fruit herein described may vary in slight detail due to climatic and soil conditions under which the variety may be grown; the present description being of the variety as grown in the Central Valley of California, particularly near Winton, Merced County, Calif.

What is claimed is:

1. A new and distinct variety of peach tree, substantially as illustrated and described, which is of medium size, moderately vigorous growth, and a regular and very productive bearer of large, relatively uniform freestone fruit having apricot yellow flesh, the pit cavity being red which streaks into the flesh, and yellow skin partially overspread with red, the skin being tenacious to the flesh when the fruit is firm ripe; the variety being further characterized, in comparison with the Rio Oso Gem, by fruit which ripens two or three days earlier, is more symmetrical in shape, and firmer of flesh, the latter being sweeter, less fibrous, and—when cut—having substantial resistance to oxidation and resultant browning.

No references cited.

ROBERT E. BAGWILL, Primary Examiner